(12) United States Patent
Matsumoto et al.

(10) Patent No.: US 10,031,027 B2
(45) Date of Patent: Jul. 24, 2018

(54) OPTICAL NONDESTRUCTIVE TESTING METHOD AND OPTICAL NONDESTRUCTIVE TESTING APPARATUS

(71) Applicant: JTEKT CORPORATION, Osaka-shi, Osaka (JP)

(72) Inventors: Naoki Matsumoto, Okazaki (JP); Kouya Yoshida, Okazaki (JP); Ryota Umezawa, Nishio (JP); Jun Matsumoto, Okazaki (JP)

(73) Assignee: JTEKT CORPORATION, Osaka-shi (JP)

( * ) Notice: Subject to any disclaimer, the term of this patent is extended or adjusted under 35 U.S.C. 154(b) by 82 days.

(21) Appl. No.: 15/392,791

(22) Filed: Dec. 28, 2016

(65) Prior Publication Data
US 2017/0199080 A1    Jul. 13, 2017

(30) Foreign Application Priority Data

Jan. 13, 2016   (JP) ................................. 2016-004217

(51) Int. Cl.
*G01J 5/00* (2006.01)
*G01J 5/52* (2006.01)

(52) U.S. Cl.
CPC .......... *G01J 5/0096* (2013.01); *G01J 5/0007* (2013.01); *G01J 5/52* (2013.01); *G01J 2005/528* (2013.01)

(58) Field of Classification Search
CPC .......... G01J 5/0096; G01J 5/0007; G01J 5/52; G01J 11/28; G01J 11/285
See application file for complete search history.

(56) References Cited

U.S. PATENT DOCUMENTS 7,364,354 B2    4/2008   Lakestani et al.
2002/0080850 A1   6/2002   Baba

FOREIGN PATENT DOCUMENTS

JP          3265362 B2      3/2002
JP       2002-122559 A      4/2002

OTHER PUBLICATIONS

Lahiri, B.B, et al. "Quantification of defects in composites and rubber materials using active thermography." vol. 55., pp. 191-199, 2012. Infrared Physics & Technology.
(Continued)

*Primary Examiner* — Casey Bryant
(74) *Attorney, Agent, or Firm* — Oliff PLC (57) ABSTRACT

An optical nondestructive testing method includes: a laser emitting step involving emitting a heating laser from a laser output device such that the intensity of the heating laser applied to a measurement point changes sinusoidally; a laser intensity measuring step involving measuring the intensity of the heating laser by a phase difference detector; an infrared radiation intensity measuring step involving measuring, by the phase difference detector, the intensity of infrared radiation radiating from the measurement point; a phase difference measuring step involving determining, by the phase difference detector, a phase difference between the intensity of the heating laser and the intensity of the infrared radiation, and outputting the phase difference determined to a determiner from the phase difference detector; and a connection area calculating step involving determining, by the determiner, a connection area in accordance with the phase difference and phase difference-connection area correlation information.

7 Claims, 9 Drawing Sheets

(56) References Cited

OTHER PUBLICATIONS

Shin, P.H., et al. "Nondestructive inspection in adhesive-bonded joint CFRP using pulsed phase thermography." vol. 8705, pp. 1-9, 2013. Thermosense: Thermal Infrared Applications XXXV.
Waugh, R.C., et al. "Pulse phase thermography and its application to kissing defects in adhesively bonded joints." vol. 70, pp. 369-374, 2011. Applied Mechanics and Materials.
May 17, 2016 Extended Search Report issued in European Patent Application No. 17 15 0077.0.

OPTICAL NONDESTRUCTIVE TESTING METHOD AND OPTICAL NONDESTRUCTIVE TESTING APPARATUS

INCORPORATION BY REFERENCE

The disclosure of Japanese Patent Application No. 2016-004217 filed on Jan. 13, 2016 including the specification, drawings and abstract is incorporated herein by reference in its entirety.

BACKGROUND OF THE INVENTION

1. Field of the Invention

The invention relates generally to optical nondestructive testing methods and optical nondestructive testing apparatuses. More particularly, the invention relates to an optical nondestructive testing method and an optical nondestructive testing apparatus that optically nondestructively determine a connection area between connection interfaces of a first member and a second member of a measurement object connected to each other directly or connected to each other with a connector interposed therebetween.

2. Description of the Related Art

In recent years, first and second members made of various materials have been connected to each other, creating a demand for testing the state of connection between the first and second members. A conventional method for testing the state of connection involves selecting an appropriate sample from a production lot, and breaking the sample so as to check the state of connection. Thus, products in this lot are regarded as having the state of connection similar to the state of connection of the sample broken. This conventional method unfortunately requires breaking a sample in order to check the state of connection. To overcome this disadvantage, various methods are disclosed to measure connection-related physical properties without causing breakage.

U.S. Pat. No. 7,364,354 discloses a thermal diffusivity measuring method involving applying a modulated beam to a measurement spot of a unitary sample so as to determine the thermal diffusivity of the sample on the basis of the phase of the modulated beam and the phase of a temperature response from the measurement spot.

Japanese Patent Application Publication No. 2002-122559 (JP 2002-122559 A) discloses a method for measuring thermal diffusivity and interfacial thermal resistance. This method involves: providing a three-layer structure made up of upper and lower metallic thin film layers of the same type having known thermophysical property values and a nonmetallic thin film layer sandwiched between the upper and lower metallic thin film layers and having unknown thermophysical property values; heating the three-layer structure from below with pulsed light; and measuring a transient temperature rise at the upper surface of the three-layer structure. Thus, the thermal diffusivity and interfacial thermal resistance of the three-layer structure are measured simultaneously.

Japanese Patent No. 3265362 discloses an interfacial thermal resistance measuring method involving: pulse-heating the surface of a two-layer sample provided by stacking a first layer made of a first material and a second layer made of a second material; and observing a temperature response from the underside of the two-layer sample. Thus, interfacial thermal resistance between the first and second layers of the two-layer sample is measured. Japanese Patent No. 3265362 also discloses an interfacial thermal resistance measuring method involving: measuring a temperature response after pulse-heating the surface of a first single layer sample consisting of a first material; measuring a temperature response after pulse-heating the surface of a second single layer sample consisting of a second material; and calculating a temperature response on the assumption that no interfacial thermal resistance is generated between the first and second layers of a two-layer sample that are made of the first and second materials, respectively, and stacked one on top of another. This method further involves determining a difference between the temperature response calculated and a temperature response from the underside of the two-layer sample measured after pulse-heating the surface of the two-layer sample. Thus, interfacial thermal resistance between the first and second layers of the two-layer sample is determined from the difference between the temperature responses.

The invention disclosed in U.S. Pat. No. 7,364,354 aims at measuring the thermal diffusivity of a unitary sample but does not aim at measuring the thermal diffusivity of a connector connecting a first member and a second member. This means that the thermal diffusivity measured is unusable for determining the state of connection between first and second members of a measurement object connected to each other directly or connected to each other with a connector interposed therebetween.

The invention disclosed in JP 2002-122559 A is applicable only to a three-layer structure made up of upper and lower metallic thin film layers of the same type having known thermophysical property values and a nonmetallic thin film layer sandwiched between the upper and lower metallic thin film layers. The physical properties to be measured are the thermal diffusivity and interfacial thermal resistance of the three-layer structure. This makes it inappropriate to apply this invention to determining the state of connection between the first and second members of a measurement object connected to each other directly or connected to each other with a connector interposed therebetween.

The invention disclosed in Japanese Patent No. 3265362 requires pulse-heating the surface of a sample and measuring a temperature response from the underside of the sample. This means that heat has to be sufficiently propagated from the surface of the sample to the underside of the sample. Thus, this invention is applicable only to a sample in the form of a thin film. The physical property to be measured is the interfacial thermal resistance of a two-layer sample. This makes it inappropriate to apply this invention to determining the state of connection between the first and second members of a measurement object connected to each other directly or connected to each other with a connector interposed therebetween.

SUMMARY OF THE INVENTION

An object of the invention is to provide an optical nondestructive testing method and an optical nondestructive testing apparatus that nondestructively determine a connection area between connection interfaces of a first member and a second member of a measurement object connected to each other directly or connected to each other with a connector interposed therebetween, so as to determine the state of connection between the first member and the second member.

An aspect of the invention provides an optical nondestructive testing method for determining a connection area between connection interfaces of a first member and a second member of a measurement object connected to each other directly or connected to each other with a connector interposed therebetween. The method involves applying a heating laser to a measurement point on a surface of the first member of the measurement object. The connection area is determined in accordance with the information on the heating laser and the information on a heated state of the measurement object obtained from the measurement point. The method includes; preparing a laser output device, a phase difference detector, and a determiner; emitting the heating laser from the laser output device such that an intensity of the heating laser applied to the measurement point changes sinusoidally; measuring the sinusoidally changing intensity of the heating laser by the phase difference detector; measuring, by the phase difference detector, a sinusoidally changing intensity of infrared radiation radiating from the measurement point; determining, by the phase difference detector, a phase difference between the sinusoidally changing intensity of the heating laser measured and the sinusoidally changing intensity of the infrared radiation measured, and outputting the phase difference determined to the determiner from the phase difference detector; and determining, by the determiner, the connection area in accordance with the phase difference received by the determiner and the phase difference-connection area correlation information stored in the determiner. The phase difference-connection area correlation information indicates a correlation between the phase difference and the connection area for the measurement object.

The method according to the above aspect determines the connection area in accordance with the phase difference-connection area correlation information stored in advance in association with the measurement object and the phase difference between the sinusoidally changing intensity of the heating laser and the sinusoidally changing intensity of the infrared radiation. This enables nondestructive and suitable determination of not only the connection area between the connection interfaces of the first and second members connected to each other directly but also the connection area between the connection interfaces of the first and second members connected to each other with a connector interposed therebetween.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Embodiments of the invention will be described below with reference to the accompanying drawings. An optical nondestructive testing apparatus 1 according to a first embodiment of the invention and an optical nondestructive testing apparatus 1A according to a second embodiment of the invention described below each determine a connection area between connection interfaces of a first member 51 and a second member 52 of a measurement object 50. The first member 51 and the second member 52 are connected to each other with solder 53. The optical nondestructive testing apparatus 1 and the optical nondestructive testing apparatus 1A each apply a heating laser to a measurement point SP on the surface of the first member 51 of the measurement object 50. The intensity of the heating laser changes sinusoidally. The optical nondestructive testing apparatus 1 and the optical nondestructive testing apparatus 1A each determine the connection area between the connection interfaces of the first member 51 and the second member 52 in accordance with information on the heating laser and information on the heated state of (or a temperature response from) the measurement object 50 obtained from the measurement point SP. As used herein, the tent "connection interface of the first member 51" may refer to a planar region of the first member 51 connected to the solder 53, and the term "connection interface of the second member 52" may refer to a planar region. of the second member 52 connected to the solder 53. The temperature response obtained from the measurement point SP is significantly influenced by the smaller one of the connection interfaces.

Figure 4:
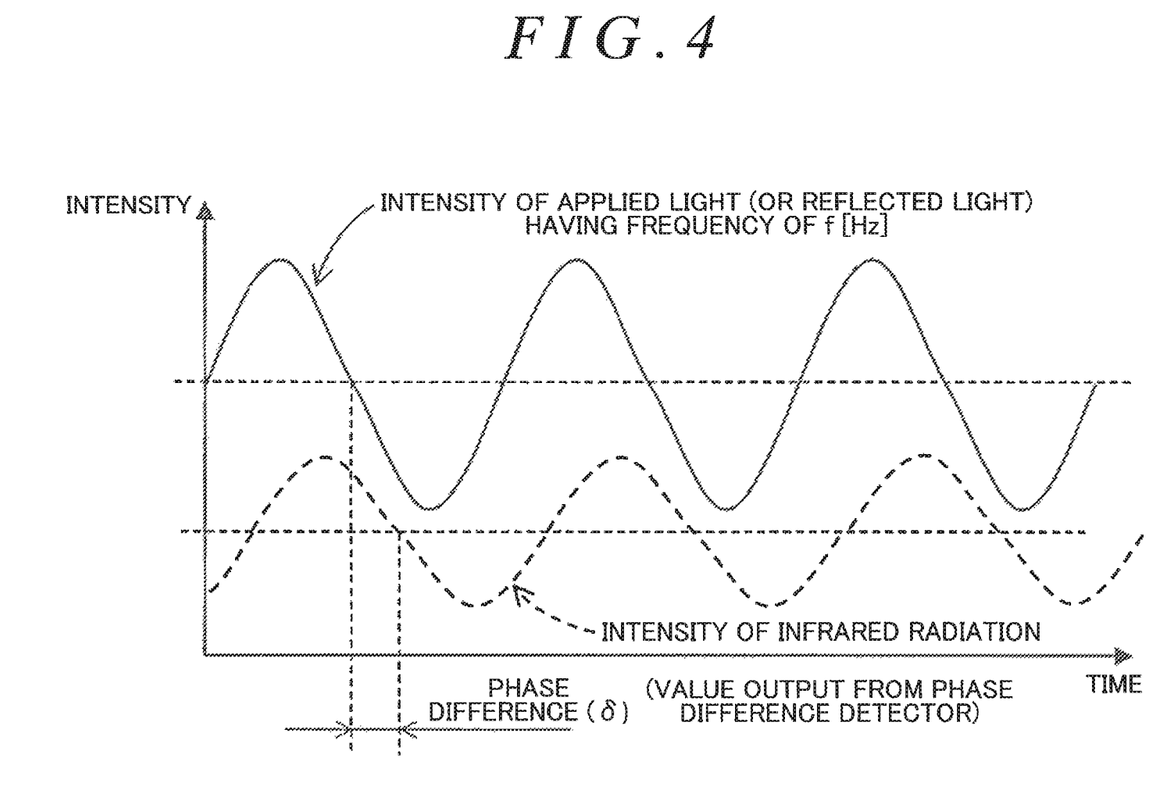
FIG. 4 is a graph illustrating an example of the intensity of applied light and an example of the intensity of infrared radiation received by the phase difference detector, and an example of a phase difference measured.

The information on the heating laser indicates the intensity of the heating laser applied to the measurement point SP. As indicated by the continuous line in FIG. 4, for example, the intensity of the heating laser changes sinusoidally with time. The information on the heated state of the measurement object 50 obtained from the measurement point SP indicates the temperature response from the measurement point SP detected on the basis of infrared radiation radiating from the measurement point SP. As indicated by the dashed line in FIG. 4, for example, the temperature response from the measurement point SP is the temperature of the measurement point SP that changes sinusoidally with time. As illustrated in FIG. 4, a phase difference ($\delta$) is determined from the sinusoidally changing intensity of the heating laser and the sinusoidally changing temperature of the measurement point SP. Thus, the connection area is determined in accordance with the phase difference ($\delta$).

First, an overall arrangement of the optical nondestructive testing apparatus 1 according to the first embodiment will be described with reference to FIG. 1. The optical nondestructive testing apparatus 1 according to the first embodiment is of the type that changes the intensity of a laser beam itself emitted from a laser light source (i.e., a semiconductor laser light source 21 in this example) and detects the intensity of the laser beam directly. The optical nondestructive testing apparatus 1 includes a laser output device 27, a condenser 10 (which is a reflecting objective lens in the examples illustrated in FIGS. 1 and 2), a laser intensity detector 41, an infrared radiation intensity detector 31, a phase difference detector 60, and a determiner 70. The following description is based on the assumption that the first member 51 is an electronic component (e.g., a chip type element), and the second member 52 is a printed circuit board, with the first member 51 and the second member 52 connected to each other with the solder 53 (equivalent to a connector). In this example, the connection interface of the first member 51 is the surface of the first member 51 connected to the solder 53, and the connection interface of the second member 52 is the surface of the second member 52 connected to the solder 53.

The laser output device 27 includes, for example, the semiconductor laser light source 21, a collimator lens 22, and a modulation signal output device 25. The modulation signal output device 25 is an oscillator, for example. The modulation signal output device 25 generates a modulation signal whose voltage changes sinusoidally with a predetermined frequency and a predetermined amplitude in accordance with a control signal from the determiner 70. The semiconductor laser light source 21 includes an intensity adjusting input. The modulation signal is supplied from the modulation signal output device 25 to the intensity adjusting input. In accordance with the modulation signal from the modulation signal output device 25, the semiconductor laser light source 21 emits a heating laser La whose intensity changes sinusoidally. The heating laser La emitted from the semiconductor laser light source 21 is converted into parallel light through the collimator lens 22. The parallel light reaches a heating laser selective reflector 23. When the heating laser La emitted from the semiconductor laser light source 21 is parallel light, the collimator lens 22 may be removed. The intensity of the heating laser La concentrated onto the measurement point SP changes sinusoidally, and the frequency of the heating laser La is synchronous with the frequency of the modulation signal. The power of the heating laser La is adjusted such that the measurement object 50 is heated without being broken.

Figure 1:
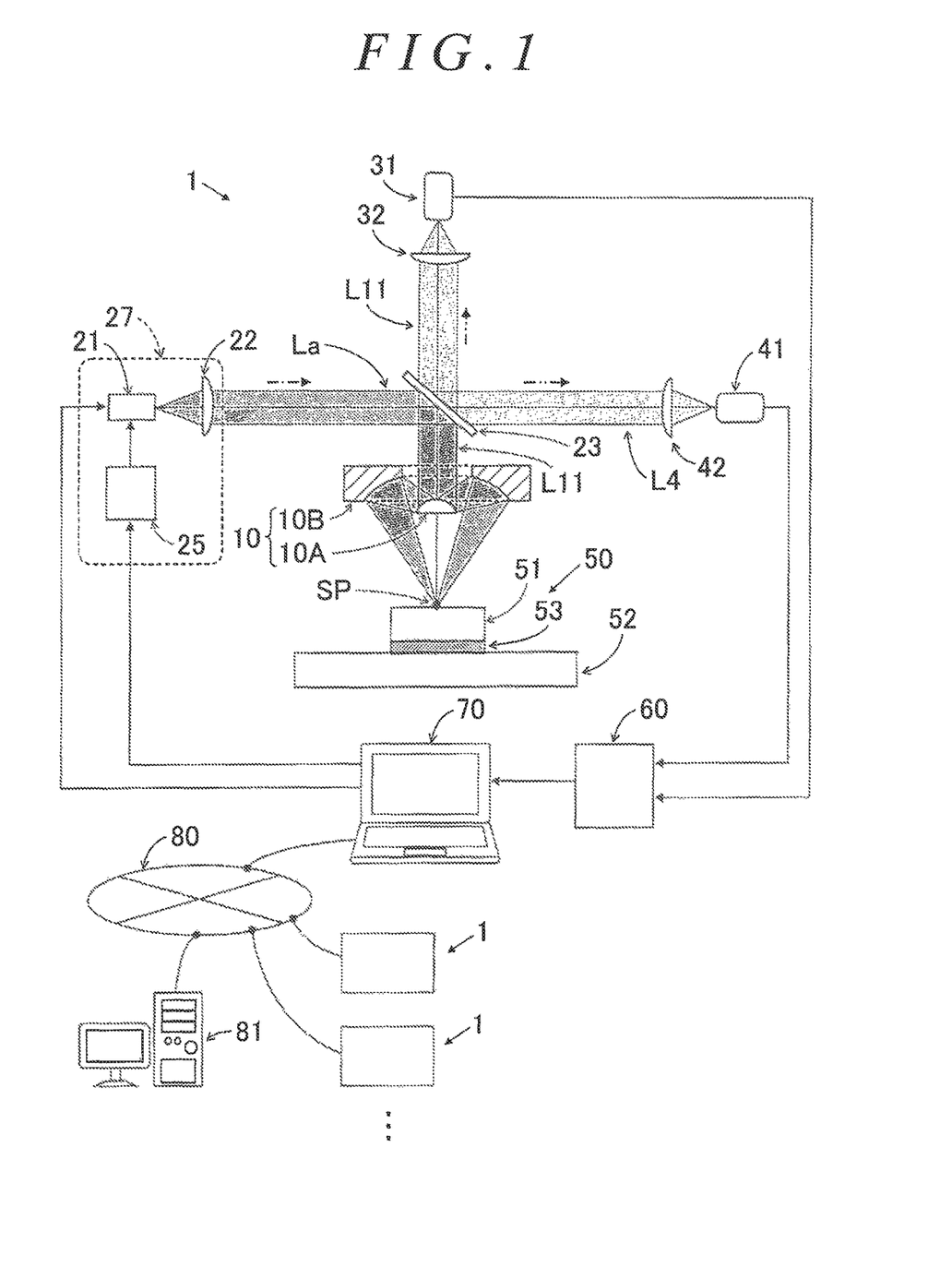
FIG. 1 is a diagram illustrating an overall arrangement of an optical nondestructive testing apparatus according to a first embodiment of the invention.

The parallel light is incident on a first side of the condenser 10 (i.e., the upper side of the condenser 10 in the example illustrated in FIG. 1) along the optical axis of the condenser 10. The condenser 10 emits the light from a second side of the condenser 10 (i.e., the lower side of the condenser 10 in the example illustrated in FIG. 1) so that the light is concentrated onto the measurement point SP provided on the surface of the first member 51 and serving as a focal point position. Light radiated and reflected from the measurement point SP (serving as the focal point position) is incident on the second side of the condenser 10. The condenser 10 converts this incident light into a first measuring beam L11 that is parallel light along the optical axis of the condenser 10, and emits the first measuring beam L11 from the first side of the condenser 10. The condenser 10 may include a condensing lens that allows light to pass therethrough and refract. The condenser 10, however, deals with light of different wavelengths. Thus, a condensing lens that causes chromatic aberrations is not so desirable. In this embodiment, the condenser 10 includes aspherical reflecting mirrors 10A and 10B so as to eliminate chromatic aberrations and cover a wide wavelength range. The condenser 10 is preferably an objective lens.

The heating laser selective reflector 23 is disposed at a location where the optical axis of the heating laser La emitted from the laser output device 27 and the optical axis of the condenser 10 intersect with each other. The heating laser selective reflector 23 is, for example, a dichroic, minor that reflects light having a wavelength equal to the wavelength of the heating laser La and allows light having a wavelength other than the wavelength of the heating laser La to pass through the heating laser selective reflector 23. In the example illustrated in FIG. 1, the heating laser selective reflector 23 allows a few percent (e.g., about two percent) of the light having a wavelength equal to the wavelength of the heating laser La to pass therethrough. The laser intensity detector 41 is disposed at a destination of a portion of the heating laser La that has passed through the heating laser selective reflector 23.

The laser intensity detector 41 is, for example, a photosensor capable of detecting optical energy corresponding to the wavelength of the heating laser La. The heating laser L4 that has passed through the heating laser selective reflector 23 and whose intensity changes sinusoidally is concentrated onto the laser intensity detector 41 through a condensing lens 42. A detection signal from the laser intensity detector 41 is amplified by a sensor amplifier, for example, and supplied to the phase difference detector 60.

The first measuring beam L11 converted into parallel light by the condenser 10 includes light applied to and reflected from the measurement point SP and infrared radiation radiating from the measurement point SP. The infrared radiation radiating from the measurement point SP has a predetermined wavelength. The infrared radiation intensity detector 31 is disposed at a destination of the first measuring beam L11.

The infrared radiation intensity detector 31 is, for example, an infrared sensor capable of detecting energy of infrared radiation having a predetermined wavelength. The infrared radiation having the predetermined wavelength and included in the first measuring beam L11 is concentrated onto the infrared radiation intensity detector 31 through a condensing lens 32. The intensity of the infrared radiation changes sinusoidally. A detection signal from the infrared radiation intensity detector 31 is amplified by a sensor amplifier, for example, and supplied to the phase difference detector 60.

The phase difference detector 60 is a lock-in amplifier, for example. The phase difference detector 60 receives the detection signal from the laser intensity detector 41 and the detection signal from the infrared radiation intensity detector 31. The detection signal from the laser intensity detector 41 sinusoidally changes in intensity and thus may also be referred to as a "sinusoidal laser detection signal". The detection signal from the infrared radiation intensity detector 31 sinusoidally changes in intensity and thus may also be referred to as a "sinusoidal infrared radiation detection signal". The phase difference detector 60 measures a phase difference between the sinusoidal laser detection signal and the sinusoidal infrared radiation detection signal, and outputs the phase difference measured to the determiner 70. The detection signal from the laser intensity detector 41 is responsive to the sinusoidally changing intensity of the heating laser La applied to the measurement point SP. The detection signal from the infrared radiation intensity detector 31 is responsive to the sinusoidally changing intensity of the infrared radiation radiating from the measurement point SP. The phase difference includes information on the connection area between the connection interfaces.

The determiner 70 is, for example, a personal computer. The determiner 70 outputs a control signal to the laser output device 27 and imports the phase difference from the phase difference detector 60. As will be described below, the determiner 70 determines the connection area between the connection interfaces in accordance with the phase difference imported and phase difference-connection area correlation information (for the measurement object 50) stored in the determiner 70. The details of the phase difference-connection area correlation information and how the connection area is determined will be described below.

Figure 7:
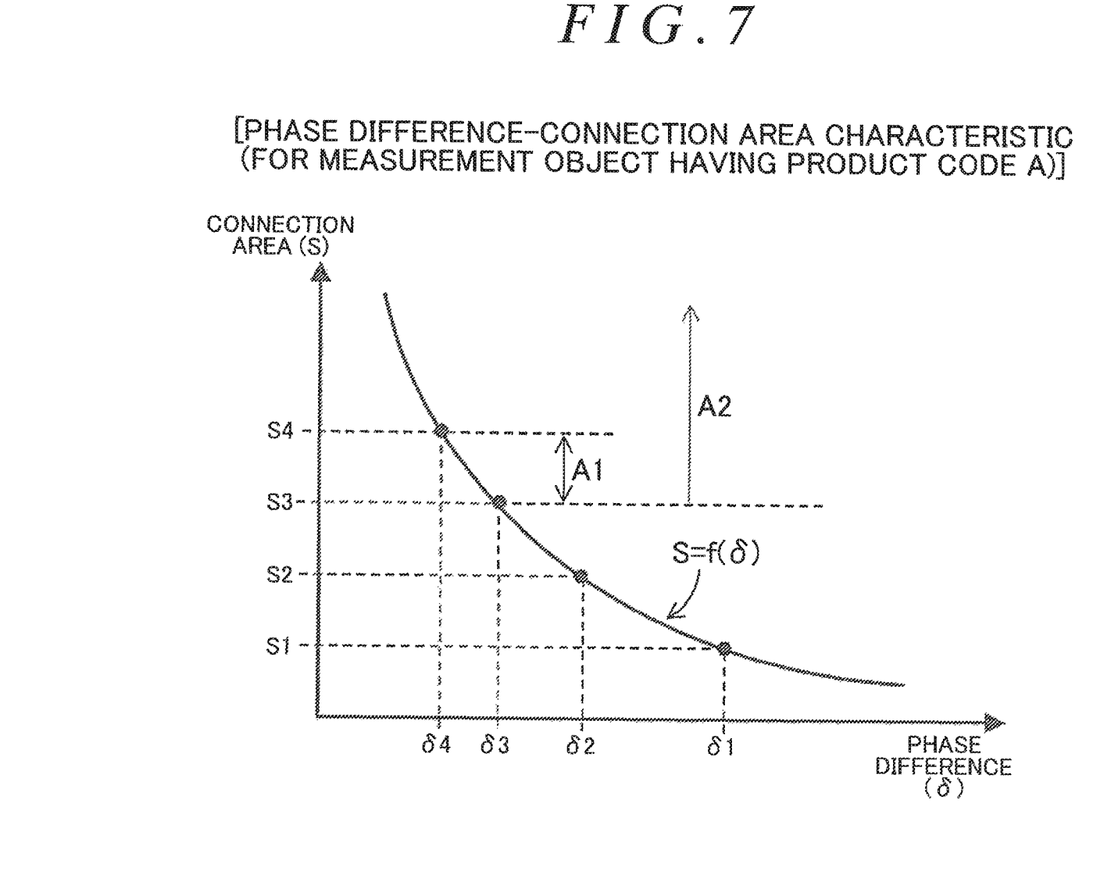
FIG. 7 is a graph illustrating exemplary phase difference-connection area correlation information based on the example illustrated in FIG. 6.

Suppose that the optical nondestructive testing apparatus 1 is installed in a facility such as a factory. In such a case, it is advantageous to connect the determiner 70 to a communication line 80 in the facility (e.g., a LAN in the facility) and deliver the phase difference-connection area correlation information (for the measurement object 50) to the determiner 70 from a delivering device (or server) 81 connected to the communication line 80. The phase difference-connection area correlation information is illustrated in FIG. 7. The determiner 70 of the optical nondestructive testing apparatus 1 receives the phase difference-connection area correlation information through the communication line 80 and stores the phase difference-connection area correlation information. When more than one optical nondestructive testing apparatus 1 is installed in a facility, this system is particularly advantageous. This is because this system enables the determiners 70 of the plurality of optical nondestructive testing apparatuses 1 to receive and store the phase difference-connection area correlation information more readily and easily than when the determiner 70 of each optical nondestructive testing apparatus 1 not connected to the communication line 80 stores the phase difference-connection area correlation information.

Figure 2:
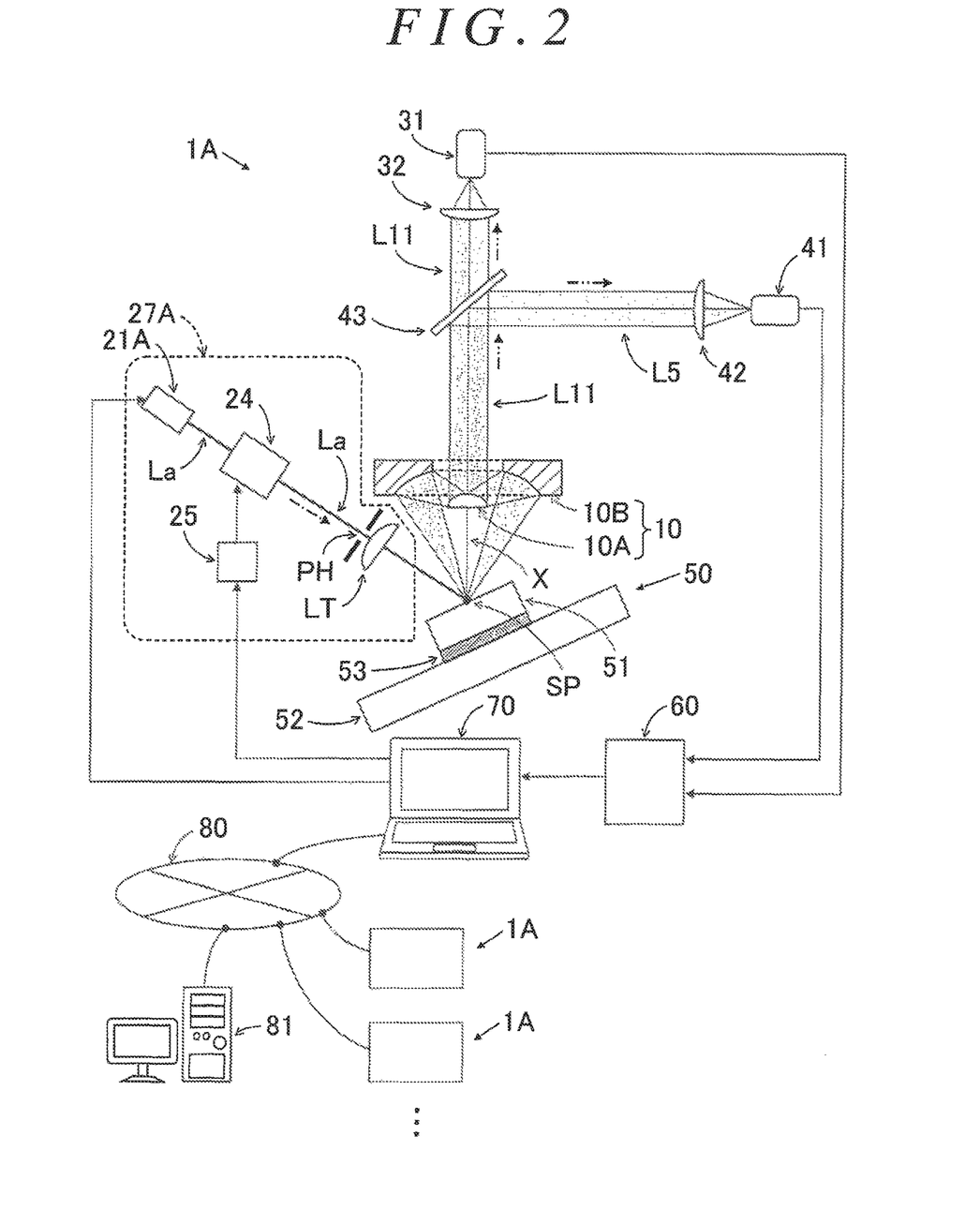
FIG. 2 is a diagram illustrating an overall arrangement of an optical nondestructive testing apparatus according to a second embodiment of the invention.

Referring to FIG. 2, an overall arrangement of the optical nondestructive testing apparatus 1A according to the second embodiment will be described below. The optical nondestructive testing apparatus 1A according to the second embodiment is not of the type that changes the intensity of a laser beam itself emitted from a laser light source 21A but is of the type that causes the laser beam emitted to be refracted at various angles so as to increase or reduce the amount of the laser beam passing through a pinhole PH and detect the intensity of the laser beam reflected from the measurement point SP. The optical nondestructive testing apparatus 1A according to the second embodiment differs from the optical nondestructive testing apparatus 1 according to the first embodiment in that the laser output device 27 is replaced by a laser output device 27A configured to emit a linear heating laser La, no heating laser selective reflector 23 is provided, and a reflected light selective reflector 43 is added. The following description mainly discusses these differences. Features of the second embodiment other than these differences are as explained for the first embodiment, and the description thereof will be omitted. In the example illustrated in FIG. 2, the angle of inclination of the measurement object 50 is set in accordance with the incident angle of the heating laser La incident on the measurement object 50 and the angle of reflection of the heating laser La from the measurement point SP (i.e., the angle of an optical axis X of the heating laser La reflected from the measurement point SP). The measurement object 50 includes the first member 51 and the second member 52 connected to each other with the solder 53.

The laser output device 27A includes, for example, the laser light source 21A to emit the linear heating laser La, an acousto-optical modulator 24, and the modulation signal output device 25. The laser output device 27A emits the heating laser La in accordance with a control signal from the determiner 70 such that the intensity of the heating laser La applied to the measurement point SP changes sinusoidally. The modulation signal output device 25 is, for example, an oscillator. The modulation signal output device 25 generates a modulation signal whose voltage changes sinusoidally with a predetermined frequency and a predetermined amplitude in accordance with a control signal from the determiner 70. The linear heating laser La emitted from the laser light source 21A is applied to the acousto-optical modulator 24 and diffracted (or refracted) by the acousto-optical modulator 24 as will be described below. The acousto-optical modulator 24 includes an electrooptical modulator (EOM) device and/or a surface acoustic wave (SAW) device. When light is passed through a piezoelectric crystal, for example, the electrooptical modulator device applies an electric field or an ultrasonic wave thereto in accordance with the modulation signal from the modulation signal output device 25 so as to produce a piezoelectric effect, thus changing the refractive index in the piezoelectric 10 crystal. The heating laser La refracted is derived as diffracted light. The heating laser La emitted from the acousto-optical modulator 24 is refracted periodically at very slight angles of refraction, so that the heating laser La passes through the pinhole PH in a laser light-shielding member and is then concentrated onto the measurement point SP through an objective lens LT. In other words, when the heating laser La passes through the pinhole PH while being refracted periodically at various angles of refraction, the amount of the heating laser La passing through the pinhole PH changes periodically. This results in a sinusoidal change in the intensity of the heating laser La applied to the measurement point SP and synchronization of the frequency of the heating laser La with the frequency of the modulation signal. The power of the heating laser La is adjusted such that the measurement object 50 is heated without being broken.

The reflected light selective reflector 43 is disposed somewhere along an optical path of the first measuring beam L11. The first measuring beam L11 includes light applied to and reflected from the measurement point SP and infrared radiation radiated from the measurement point SP. The reflected light selective reflector 43 is, for example, a dichroic mirror that reflects light having a wavelength equal to the wavelength of the light reflected from the measurement point SP (i.e., the wavelength of the heating laser La reflected from the measurement point SP) and allows light having a wavelength other than the wavelength of the reflected light to pass through the reflected light selective reflector 43. The condensing lens 42 and the laser intensity detector 41 are disposed at destinations of reflected light L5 reflected from the reflected light selective reflector 43. The condensing lens 42 and the laser intensity detector 41 function as explained for the first embodiment, and the description thereof will be omitted.

Referring to the flowchart illustrated in FIG. 3A and 3B, an example of a processing procedure to be executed by the determiner 70 and the phase difference detector 60 will be described below. The following description, including the description of the processing procedure to be executed by the determiner 70 and the phase difference detector 60, applies to both of the first embodiment and the second embodiment. Activation of the determiner 70 by an operator, for example, causes the phase difference detector 60 to activate in conjunction therewith. Thus, the determiner 70 advances the process to step S15, and the phase difference detector 60 advances the process to step S140.

The following description first discusses how steps S15 to S35 are executed by the determiner 70. In step S15, the determiner 70 determines whether there is data to be received by the determiner 70 through the communication line 80. When there is data to be received by the determiner 70 (i.e., when the answer is Yes), the process goes to step S20. When there is no data to be received by the determiner 70 (i.e., when the answer is No), the process goes to step S30.

In step S20, the determiner 70 receives data through the communication line 80. The process then goes to step S25. In step S25, the determiner 70 determines whether the data reception has ended. When the data reception has ended (i.e., when the answer is Yes), the process goes to step S30. When the data reception has not ended (i.e., when the answer is No), the process returns to step S20.

The data received by the determiner 70 is the phase difference-connection area correlation information delivered from the delivering device 81 illustrated in FIGS. 1 and 2. FIG. 7 illustrates an example of the phase difference-connection area correlation information. The phase difference-connection area correlation information includes a product code (for the measurement object 50), a phase difference-connection area characteristic graph, e.g., the graph illustrated in FIG. 7, a regression equation f(δ), e.g., a regression equation obtained from the graph illustrated in FIG. 7, a minimum allowable area, and a maximum allowable area. In one example, the delivering device 81 delivers the phase difference-connection area correlation information at predetermined times (e.g., every time the product code of the measurement object 50 to be tested in a facility changes or every time data included in the phase difference-connection area correlation information changes). The determiner 70 receives the phase difference-connection area correlation information from the delivering device 81 through the communication line 80, and stores the received phase difference-connection area correlation information in association with the product code.

More than one measurement object 50 may be tested. In this case, the first members 51 and the second members 52 of the measurement objects 50 may be made of different materials and/or may have different sizes. Some of the measurement objects 50 may have a connector between the first member 51 and the second member 52, and the other measurement objects 50 may have no connector between the first member 51 and the second member 52. Accordingly, the measurement objects 50 are distinguished from each other by the product codes. In accordance with the product codes, the measurement objects 50 are each associated with data, such as a phase difference-connection area characteristic graph, a regression equation f(δ), a minimum allowable area, and a maximum allowable area. The details of these pieces of data will be described below.

Figure 3A:
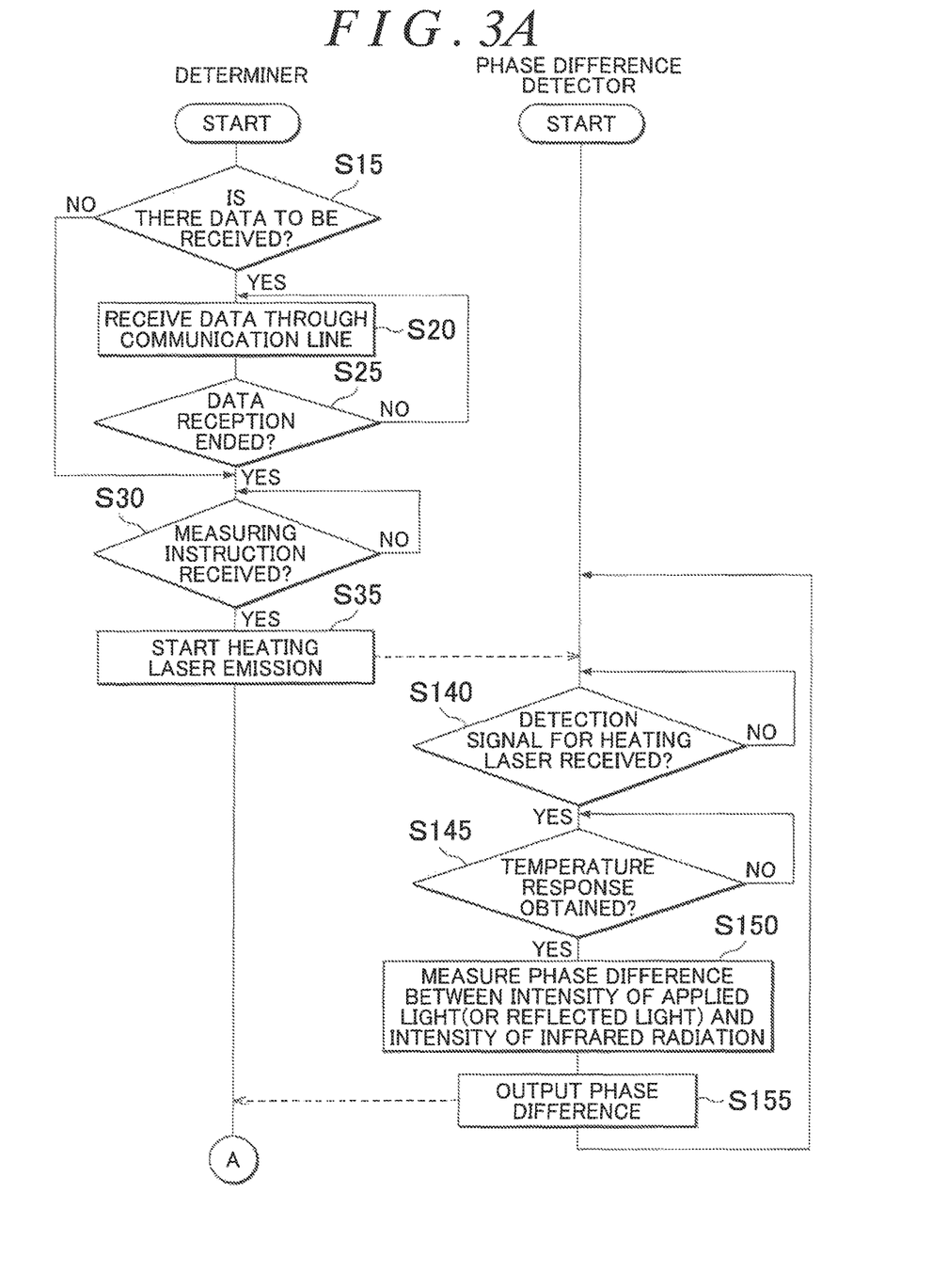
FIGS. 3A and 3B is a flowchart illustrating an example of a processing procedure to be executed by a determiner and a phase difference detector.
Figure 3B:
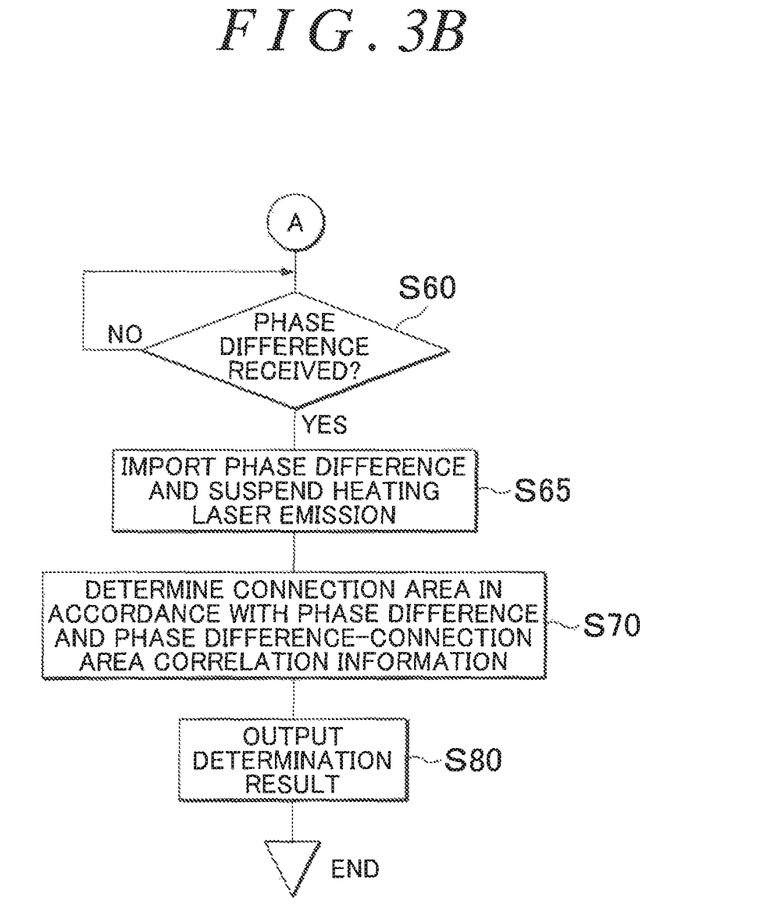

As used herein, the term "minimum allowable area" refers to a minimum possible area determined (area obtained by the determining the connection area) to be normal for the connection area calculated in step S70 of the flowchart in FIGS. 3A and 3B. As used herein, the term "maximum allowable area" refers to a maximum possible area. determined to be normal for the connection area calculated in step S70 of the flowchart in FIGS. 3A and 3B. Specifically, the determiner 70 determines the state of connection between the first member 51 and the second member 52 to be normal When the connection area calculated is between the minimum allowable area and the maximum allowable area, inclusive. The determiner 70 determines the state of connection between the first member 51 and the second member 52 to be abnormal when the connection area calculated is smaller than the minimum allowable area or larger than the maximum allowable area. The determiner 70 may alternatively determine the state of connection to be normal when the connection area calculated is equal to or larger than the minimum allowable area without using the maximum allowable area for this determination.

In step S30, the determiner 70 determines whether the determiner 70 has received a measuring instruction from the operator. When the determiner 70 has received the measuring instruction (i.e., when the answer is Yes), the process goes to step S35. When the determiner 70 has received no measuring instruction (i.e., when the answer is No), the process repeats step S30. The operator enters the product code in providing the measuring instruction to the determiner 70. The operator enters the product code using an input device, such as a keyboard or a bar code reader. When a bar code corresponding to the product code is assigned to the measurement object 50, the operator enters the product code using a bar code reader.

In step S35, the determiner 70 outputs a control signal to the laser output device 27 (or the laser output device 27A). In accordance with the control signal received, the laser output device 27 (or the laser output device 27A) emits the heating laser La such that the intensity of the heating laser La applied to the measurement point SP changes sinusoidally with a predetermined frequency. Upon completing step S35, the determiner 70 waits for reception of a phase difference from the phase difference detector 60 in step S60. Step S35 is equivalent to a "laser emitting step" involving emitting the heating laser such that the intensity of the heating laser applied to the measurement point changes sinusoidally.

The following description discusses how steps S140 to S155 are executed by the phase difference detector 60. In step S140, the phase difference detector 60 determines whether the phase difference detector 60 has received a detection signal from the laser intensity detector 41. Specifically, the phase difference detector 60 determines whether the phase difference detector 60 has received, from the laser intensity detector 41, a detection signal for the heating laser La that is the light applied to the measurement point SP (see FIG. 1) or the light reflected from the measurement point SP (see FIG. 2). When the phase difference detector 60 has received the detection signal for the heating laser La (i.e., when the answer is Yes), the process goes to step S145. When the phase difference detector 60 has received no detection signal for the heating laser La (i.e., when the answer is No), the process repeats step S140.

In step S145, the phase difference detector 60 determines whether the phase difference detector 60 has obtained a temperature response based on a detection signal from the infrared radiation intensity detector 31. When the phase difference detector 60 has obtained the temperature response (i.e., when the answer is Yes), the process goes to step S150. When the phase difference detector 60 has received no temperature response (i.e., when the answer is No), the process repeats step S145. The phase difference detector 60 may alternatively determine whether the phase difference detector 60 has obtained the temperature response by determining whether the infrared radiation intensity detector 31 has received infrared radiation having a predetermined wavelength.

In step S150, the phase difference detector 60 measures, in accordance with the detection signal from the laser intensity detector 41, the intensity of the light applied to the measurement point SP (in the case of the arrangement illustrated in FIG. 1) or the light reflected from the measurement point SP (in the case of the arrangement illustrated in FIG. 2). The applied light and the reflected light each sinusoidally change in intensity and have a predetermined frequency. The continuous line in FIG. 4 indicates an example of the intensity of the applied light (or the reflected light) measured. In accordance with the detection signal from the infrared radiation intensity detector 31, the phase difference detector 60 measures the intensity of the infrared radiation that changes sinusoidally. The dashed line in FIG. 4 indicates an example of the intensity of the infrared radiation measured. The phase difference detector 60 measures a phase difference δ between the sinusoidally changing intensity of the applied light (or the reflected light) measured and the sinusoidally changing intensity of the infrared radiation measured (see FIG. 4). The process then goes to step S155.

Step S150 includes a "laser intensity measuring step" involving measuring the sinusoidally changing intensity of the heating laser having a predetermined frequency and reflected from the measurement point or the sinusoidally changing intensity of the heating laser having a predetermined frequency and applied to the measurement point. Step S150 further includes an "infrared radiation intensity measuring step" involving measuring the sinusoidally changing intensity of infrared radiation radiating from the measurement point. Step S150 and step S155 include a "phase difference measuring step" involving determining the phase difference between the sinusoidally changing intensity of the heating laser (i.e., the reflected light or the applied light) measured and the sinusoidally changing intensity of the infrared radiation measured, and outputting the phase difference determined to the determiner.

In step S155, the phase difference detector 60 outputs the phase difference δ measured to the determiner 70. The process then returns to step S140.

The following description discusses how steps S60 to S80 are executed by the determiner 70. In step S60, the determiner 70 determines whether the determiner 70 has received the phase difference from the phase difference detector 60. When the determiner 70 has received the phase difference (i.e., when the answer is Yes), the process goes to step S65. When the determiner 70 has received no phase difference (i.e., when the answer is No), the process repeats step S60.

In step S65, the determiner 70 imports the phase difference and outputs a control signal to the laser output device 27 (or the laser output device 27A) so as to suspend the emission of the heating laser La from the laser output device 27 (or the laser output device 27A). The process then goes to step S70.

In step S70, the determiner 70 determines the connection area in accordance with the phase difference imported and the phase difference-connection area correlation information (for the measurement object 50) stored in the determiner 70 or an external memory. The process then goes to step S80. The phase difference-connection area correlation information indicates the correlation between the phase difference and the connection area. The details of the phase difference-connection area correlation information and the details of how the connection area is determined will be described. below. Step S70 is equivalent to a "connection area calculating step" involving determining the connection area in accordance with the phase difference and the phase difference-connection area correlation information (for the measurement object). To accomplish this step, the determiner 70 includes a converter (or a converting circuit) to convert the phase difference into the connection area in accordance with the phase difference and the phase difference-connection area correlation information. The phase difference-connection area correlation information includes at least one of a phase difference-connection area characteristic and a regression equation as will be described below.

Figure 8:
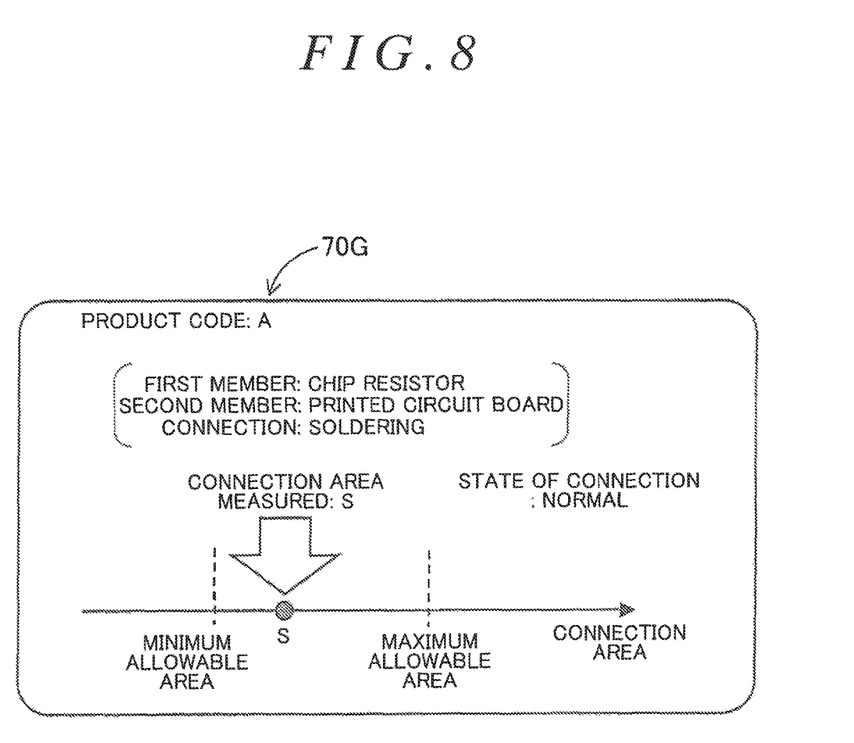
FIG. 8 is a diagram illustrating an example of a determination result.

In step S80, the determiner 70 outputs a determination result indicating whether the state of connection between the first member 51 and the second member 52 is normal or abnormal in accordance with the connection area determined in step S70 (see FIG. 8). Thus, the process comes to an end. In one example, the determiner 70 determines the state of connection to be normal when the connection area determined is within a predetermined range, i.e., between the minimum allowable area and the maximum allowable area, inclusive. In another example, the determiner 70 determines the state of connection to be normal when the connection area determined is equal to or larger than the minimum allowable area. Step S80 is equivalent to a "determination result outputting step" involving outputting the determination result indicating whether the connection area determined is within a predetermined range set in advance or whether the connection area determined is equal to or larger than a predetermined area set in advance. To accomplish this step, the determiner 70 includes an output device (or an output circuit) to output the determination result indicating whether the connection area determined is within the predetermined range set in advance or whether the connection area determined is equal to or larger than the predetermined area set in advance. The details of how the determination result is output will be described below.

Figure 5:
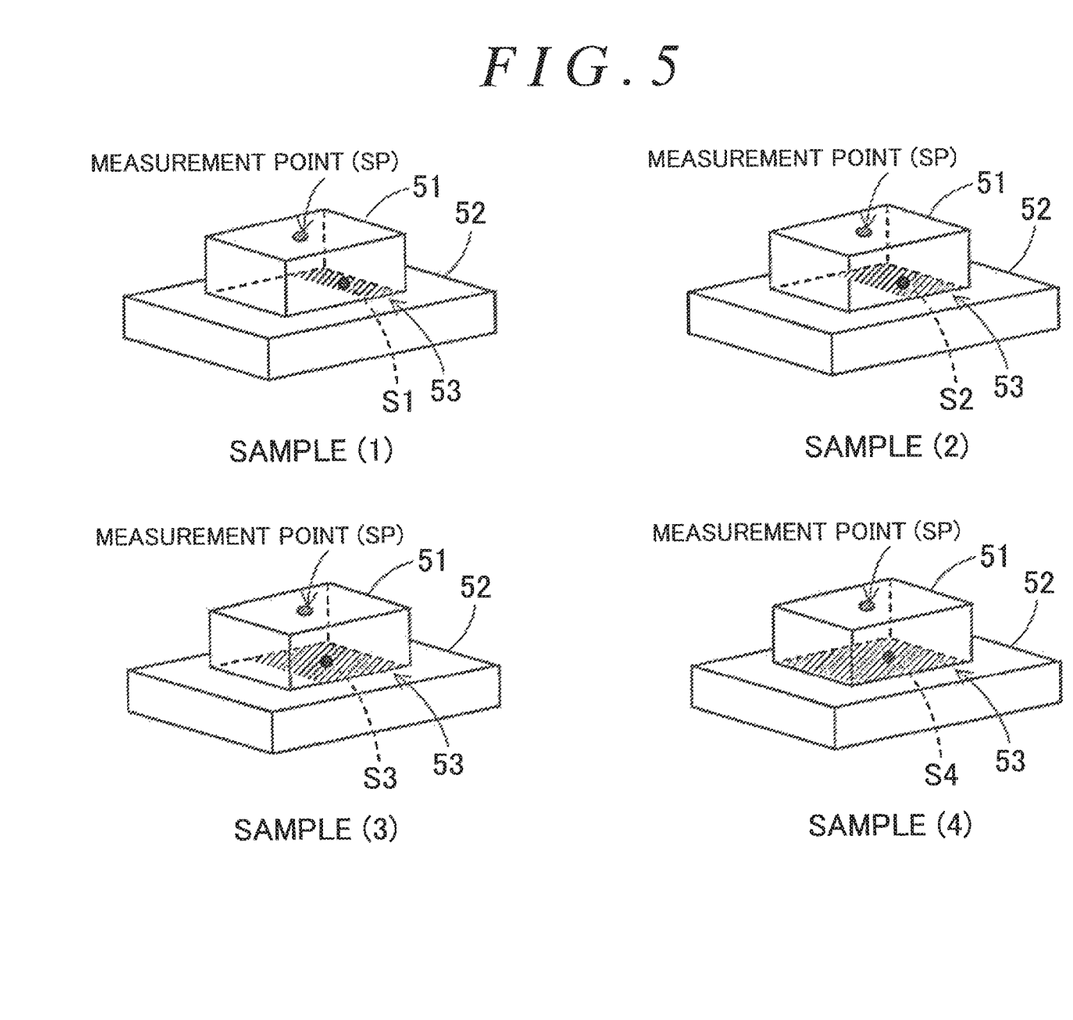
FIG. 5 is a diagram illustrating examples of samples different only in connection area.
Figure 6:
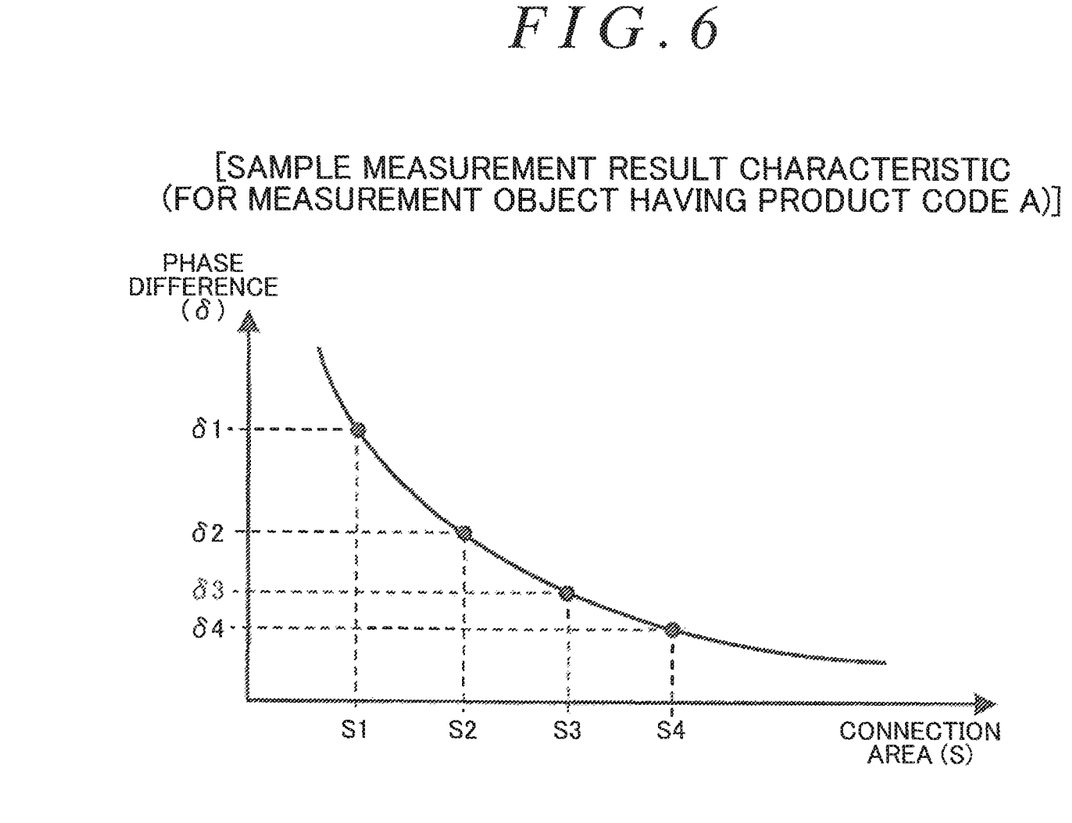
FIG. 6 is a graph illustrating an example of the relationship between the connection area (known) and phase difference (measured value) of each sample.

The following description discusses an example of a method for creating phase difference-connection area correlation information. As illustrated in FIG. 5, a plurality of samples different only in connection area between the first member 51 and the second member 52 are prepared for the measurement object 50 having a specific product code (e.g., A in this example). In the example illustrated in FIG. 5, four samples, i.e., samples (1) to (4), are prepared, and connection areas S1 to S4 of the samples (1) to (4) are known in advance. Each sample is subjected to optical nondestructive testing using the optical nondestructive testing apparatus 1 illustrated in FIG. 1 or the optical nondestructive testing apparatus 1A illustrated in FIG. 2 so as to measure the phase difference (δ). In this example, a phase difference δ1 is measured for the sample (1) having the connection area S1, a phase difference δ2 is measured for the sample (2) having the connection area S2, a phase difference δ3 is measured for the sample (3) having the connection area S3, and a phase difference δ4 is measured for the sample (4) having the connection area S4. As illustrated in FIG. 6, the use of the plurality of samples different only in the connection area between the first member 51 and the second member 52 enables acquisition of a sample measurement result characteristic of the measurement object 50 having the product code A. Instead of preparing a plurality of samples and acquiring a sample measurement result characteristic therefrom, a characteristic equivalent to the sample measurement result characteristic illustrated in FIG. 6 may be acquired by conducting a plurality of simulations.

As illustrated in FIG. 7, the phase difference-connection area characteristic of the measurement object 50 having the product code A is obtainable from the sample measurement result characteristic acquired (or the characteristic acquired by conducting simulations). From the phase difference-connection area characteristic of the measurement object 50 having the product code A, a regression equation f(δ) may be obtained. A connection area (S) varying in relation to the phase difference (δ) is derived from the regression equation f(δ). The phase difference-connection area characteristic may be provided in the form of a graph as illustrated in FIG. 7 or may be provided in the form of a look-up table that presents connection areas for various phase differences. The phase difference-connection area correlation information stored in the determiner 70 includes at least one of the phase difference-connection area characteristic and the regression equation. This enables the determiner 70 to determine the connection area from the phase difference using at least one of the phase difference-connection area characteristic obtained for the measurement object 50 and the regression equation obtained for the measurement object 50. Such a method makes it possible to determine connection areas more accurately and easily for various measurement objects 50, such as the measurement object 50 including the first member 51 and the second member 52 connected to each other directly by welding, for example, the measurement object 50 including the first member 51 and the second member 52 connected to each other with a connector, such as the solder 53, interposed therebetween, and the measurement object 50 including the first member 51 and the second member 52 that are not made of a single substance. In one example, assuming that the connection area S3 is set to be the minimum allowable area S3 and the connection area S4 is set to be the maximum allowable area S4 as illustrated in FIG. 7, the state of connection may be determined to be normal when the connection area Obtained is within a predetermined area range A1, i.e., between the minimum allowable area S3 and the maximum allowable area S4, inclusive. In another example, assuming that the connection area S3 is set to be the minimum allowable area S3 as illustrated in FIG. 7, the state of connection may be determined to be normal when the connection area obtained is within a range A2, i.e., equal to or larger than the minimum allowable area S3. In still another example, assuming that the phase difference is not converted into the connection area, the state of connection may be determined to be normal when the phase difference is between the phase difference δ3 associated with the minimum allowable area S3 and the phase difference δ4 associated with the maximum allowable area S4, inclusive, or may be determined to be normal when the phase difference is equal to or smaller than the phase difference δ3 associated with the minimum allowable area S3.

FIG. 8 illustrates exemplary determination result information 70G presented on a display (such as a monitor) of the determiner 70. The determination result information 70G includes the connection area S determined. In this example, the phase difference-connection area correlation information stored in the determiner 70 includes a product code, a minimum allowable area, a maximum allowable area, and at least one of a phase difference-connection area characteristic and a regression equation. The minimum allowable area in FIG. 8 is determined on the basis of the phase difference-connection area correlation information stored in the determiner 70 and the product code entered in step S30. The maximum allowable area in FIG. 8 is determined on the basis of the phase difference-connection area correlation information stored in the determiner 70 and the product code entered in step S30. The determiner 70 determines the state of connection to be normal when the connection area S calculated is between the minimum allowable area and the maximum allowable area, inclusive. The determiner 70 determines the state of connection to be abnormal when the connection area S calculated is smaller than the minimum allowable area or larger than the maximum allowable area. In the example illustrated in FIG. 8, the state of connection is determined to be normal. An operator easily recognizes whether the state of connection of the measurement object 50 is normal or abnormal by looking at the determination result information 70G.

Although in the above example, determination results are output using software that mainly handles digital values, determination results may be output in various other manners. In one example, a hardware voltage comparator that handles analog values may be used. In this example, the voltage comparator receives a voltage responsive to a minimum allowable area and a voltage responsive to a connection area determined, and compares these voltages. When the voltage responsive to the connection area determined is equal to or larger than the voltage responsive to the minimum allowable area, the voltage comparator may output an ON signal that causes a lamp to be lit up or a sound, such as a chime, to be emitted, indicating that the state of connection is normal. Thus, the output device (or output circuit) to output determination results may have various configurations, such as a software configuration, a hardware configuration, a digital configuration, and an analog configuration.

The optical nondestructive testing apparatuses and methods according to the embodiments of the invention nondestructively determine the connection area between the connection interfaces of the first member 51 and the second member 52 of the measurement object 50 connected to each other directly or connected to each other with a connector interposed therebetween.

As previously described, the optical nondestructive testing apparatuses and methods according to the embodiments of the invention determine the connection area in accordance with the phase difference between the intensity of infrared radiation and the intensity of light reflected from the measurement point SP (or light applied from the laser output device 27 or 27A). This feature makes it unnecessary to determine an absolute temperature (or absolute intensity) from the infrared radiation radiating from the measurement point SP, and thus simply requires detecting a sinusoidally changing intensity of the infrared radiation, i.e., a sinusoidal waveform resulting from a change in the intensity of the infrared radiation. This waveform requires no amplitude accuracy. This feature also makes it unnecessary to determine an absolute intensity of the light reflected from the measurement point SP (or the light applied from the laser output device 27 or 27A), and thus simply requires detecting a sinusoidally changing intensity of the reflected light (or the applied light), i.e., a sinusoidal waveform resulting from a change in the intensity of the reflected light (or the applied light). This waveform requires no amplitude accuracy. Accordingly, this feature makes it possible to determine a connection area without being influenced by the condition of the surface of the first member 51 on which the measurement point SP is provided. This results in the reduction of error occurrence caused by the influence of disturbances, leading to highly accurate determination of a connection area. The optical nondestructive testing apparatuses and methods according to the embodiments of the invention use the phase difference-connection area correlation information for the measurement object 50 obtained from a plurality of samples or by conducting a plurality of simulations. This feature makes it possible to determine connection areas more accurately and easily for various measurement objects 50, such as the measurement object 50 including the first member 51 and the second member 52 connected to each other directly by welding, for example, the measurement object 50 including the first member 51 and the second member 52 connected to each other with a connector, such as the solder 53, interposed therebetween, and the measurement object 50 including the first member 51 and the second member 52 that are not made of a single substance.

Various modifications, additions, and deletions may be made to, for example, the configurations or outer appearances of the optical nondestructive testing apparatuses according to the embodiments of the invention and the processing procedures of the optical nondestructive testing methods according to the embodiments of the invention without departing from the scope of the invention.

The description of the embodiments is based on the assumption that the first member 51 is an electronic component, and the second member 52 is a printed circuit board, with the first member 51 and the second member 52 connected to each other with the solder (connector) 53. The invention, however, is applicable to various measurement objects, such as a measurement object including a first member that is a bonding wire used in semiconductor technology and a second member that is a semiconductor chip frame, with the bonding wire bonded to the chip frame by ultrasonic compression. In other words, the first member 51 may be made of any material, the second member 52 may be made of any material, the connector is optional, and the first member 51 and the second member 52 may be connected to each other in any manner. Thus, the invention is applicable to determining connection areas for various measurement objects.

The heating laser La may be any of various lasers, such as an infrared laser, an ultraviolet laser, and a visible laser.

The description of the embodiments is based on the assumption that the phase difference detector 60 and the determiner 70 are separate devices. Alternatively, the phase difference detector 60 and the determiner 70 may be combined in one device.

The invention claimed is:

1. An optical nondestructive testing method for determining a connection area between connection interfaces of a first member and a second member of a measurement object connected to each other directly or connected to each other with a connector interposed therebetween, the method involving applying a heating laser to a measurement point on a surface of the first member of the measurement object, the connection area being determined in accordance with information on the heating laser and information on a heated state of the measurement object obtained from the measurement point, the method comprising:
 preparing a laser output device, a phase difference detector, and a determiner;
 emitting the heating laser from the laser output device such that an intensity of the heating laser applied to the measurement point changes sinusoidally;
 measuring the sinusoidally changing intensity of the heating laser by the phase difference detector;
 measuring, by the phase difference detector, a sinusoidally changing intensity of infrared radiation radiating from the measurement point;
 determining, by the phase difference detector, a phase difference between the sinusoidally changing intensity of the heating laser measured and the sinusoidally changing intensity of the infrared radiation measured, and outputting the phase difference determined to the determiner from the phase difference detector; and
 determining, by the determiner, the connection area in accordance with the phase difference received by the determiner and in accordance with phase difference-connection area correlation information stored in the determiner, the phase difference-connection area correlation information indicating a correlation between the phase difference and the connection area for the measurement object.

2. The optical nondestructive testing method according to claim 1, wherein
 the phase difference-connection area correlation information includes at least one of a phase difference-connection area characteristic that is a characteristic of the connection area varying in relation to the phase difference and a regression equation for deriving the connection area varying in relation to the phase difference, the phase difference-connection area characteristic and the regression equation being obtained in advance for the measurement object from a plurality of samples or by conducting a plurality of simulations.

3. The optical nondestructive testing method according to claim 1, further comprising outputting a determination result indicating whether the connection area obtained by the determining the connection area is within a predetermined range set in advance or whether the connection area obtained by the determining the connection area is equal to or larger than a predetermined area set in advance.

4. An optical nondestructive testing apparatus that determines a connection area between connection interfaces of a first member and a second member of a measurement object connected to each other directly or connected to each other with a connector interposed therebetween, the apparatus applying a heating laser to a measurement point on a surface of the first member of the measurement object, the connection area being determined in accordance with information on the heating laser and information on a heated state of the measurement object obtained from the measurement point, the apparatus comprising:
 a laser output device to emit the heating laser such that an intensity of the heating laser applied to the measurement point changes sinusoidally;
 a laser intensity detector to generate a laser intensity detection signal in accordance with the sinusoidally changing intensity of the heating laser applied to the measurement point and output the laser intensity detection signal to a phase difference detector;
 an infrared radiation intensity detector to generate an infrared radiation intensity detection signal in accordance with a sinusoidally changing intensity of infrared radiation radiating from the measurement point and output the infrared radiation intensity detection signal to the phase difference detector;
 the phase difference detector to measure the sinusoidally changing intensity of the heating laser in accordance with the laser intensity detection signal received, measure the sinusoidally changing intensity of the infrared radiation in accordance with the infrared radiation intensity detection signal received, determine a phase difference between the intensity of the heating laser measured and the intensity of the infrared radiation measured, and output the phase difference determined to a determiner; and
 the determiner to determine the connection area in accordance with the phase difference received and phase difference-connection area correlation information stored in the determiner, the phase difference-connection area correlation information indicating a correlation between the phase difference and the connection area for the measurement object.

5. The optical nondestructive testing apparatus according to claim 4, wherein
 the phase difference-connection area correlation information includes at least one of a phase difference-connection area characteristic that is a characteristic of the connection area varying in relation to the phase difference and a regression equation for deriving the connection area varying in relation to the phase difference, the phase difference-connection area characteristic and the regression equation being obtained in advance for the measurement object from a plurality of samples or by conducting a plurality of simulations.

6. The optical nondestructive testing apparatus according to claim 5, wherein
the determiner includes a converter to convert the phase difference into the connection area in accordance with the phase difference received and at least one of the phase difference-connection area characteristic and the regression equation stored in the determiner.

7. The optical nondestructive testing apparatus according to claim 4, wherein
the determiner includes an output device to output a determination result indicating whether the connection area obtained by the determining the connection area is within a predetermined range set in advance or whether the connection area obtained by the determining the connection area is equal to or larger than a predetermined area set in advance.

* * * * *